United States Patent [19]
Dlubala et al.

[11] Patent Number: 6,063,937
[45] Date of Patent: May 16, 2000

[54] METHOD OF MAKING ASCORBYL MONOPHOSPHATES

[75] Inventors: Alain Dlubala, Rixheim, France; Paul Nösberger, Birsfelden, Switzerland

[73] Assignee: Roche Vitamins Inc., Nutley, N.J.

[21] Appl. No.: 09/040,210

[22] Filed: Mar. 17, 1998

[30] Foreign Application Priority Data

Mar. 18, 1997 [EP]  European Pat. Off. ............. 97104554

[51] Int. Cl.[7] ...................................................... C07F 9/06
[52] U.S. Cl. .............................................................. 549/218
[58] Field of Search ............................................. 549/218

[56] References Cited

U.S. PATENT DOCUMENTS

| | | | |
|---|---|---|---|
| 4,179,445 | 12/1979 | Sieb et al. ........................ | 260/340.9 R |
| 4,647,672 | 3/1987 | Sieb et al. ................. | 549/222 |
| 4,999,437 | 3/1991 | Dobler et al. ............... | 549/222 |
| 5,110,950 | 5/1992 | Sieb et al. ................. | 549/222 |
| 5,420,302 | 5/1995 | Kaiser et al. .............. | 549/222 |

OTHER PUBLICATIONS

C.H. Lee, et al., Carbohydrate Res, vol. 67, pp. 127–138 (1978).

*Primary Examiner*—Amelia Owens
*Attorney, Agent, or Firm*—Mark E. Waddell; Stephen M. Haracz; Bryan Cave LLP

[57] ABSTRACT

The present invention provides a method of making alkali metal and alkaline earth metal salts of L-ascorbic acid 2-monophosphate comprising reacting a L-ascorbic acid 2-polyphosphate under alkaline conditions with an alkali metal or alkaline earth metal salt of L-ascorbic-acid in concentrated aqueous solution. The amount of the L-ascorbic acid salt is in molar excess of the polyphosphate and the pH value of the reaction medium is maintained in the range of from about 8 to about 11 wherein the reaction is carried out until substantially all of the polyphosphate has been consumed and only L-ascorbic acid 2-monophosphate salt is present. A further aspect of the present invention comprises spray drying the mixture obtained after completion of the reaction, cooling and dilution to a suitable viscosity. The product of the process according to the invention is suitable as an additive for human and animal foodstuffs; it is especially stable against oxidative and thermal degradation and has an especially high content of L-ascorbic acid monophosphate vis-à-vis polyphosphates and is accordingly primarily of use preferably for the nutritional enrichment of fish feed.

16 Claims, No Drawings

METHOD OF MAKING ASCORBYL MONOPHOSPHATES

BACKGROUND OF THE INVENTION

The present invention relates to a novel process for making alkali metal and alkaline earth metal salts of L-ascorbic acid 2-monophosphate starting from a L-ascorbic acid salt, a L-ascorbic acid 2-polyphosphate and an alkaline earth metal hydroxide as the base.

As is known, ascorbic acid (vitamin C) and its salts are used as additives for human and animal foodstuffs. However, ascorbic acid itself is temperature-and oxidation-sensitive and is decomposed to a considerable extent, for example, in the production and storage of enriched fish feed and is thus lost. The ascorbic acid phosphates in particular are, as is known, forms of ascorbic acid which are protected against oxidative and thermal degradation and are accordingly and primarily used for the nutritional enrichment of fish feed. With the use of ascorbic acid phosphates, which are substantially more stable than ascorbic acid, the problem of decomposition is almost completely eliminated and the ascorbic acid, which is active, for example, against scurvy in fish and crabs, is liberated in the host organism by the action of the enzyme phosphatase.

Two fundamentally different processes have hither to been of significance for the phosphorylation of ascorbic acid, namely phosphorylation using phosphorus oxychloride (as described, for example, in European Patent Publications 388,869 and 582,924 as well as in U.S. Pat. No. 4,179,445) and phosphorylation using polyphosphates, e.g., sodium trimetaphosphate (see, for example, U.S. Pat. Nos. 4,647,672 and 5,110,950), with a L-ascorbic acid salt being phosphorylated under basic conditions in both cases. The first process yields ascorbic acid 2-monophosphate as the main product and as byproducts mainly ascorbic acid 3-phosphate and 2-pyrophosphate as well as bis(ascorbic acid)-2,2'-diphosphate [see C. H. Lee et al., Carbohydrate Res. 67, 127–138 (1971)]. The reaction products require complicated purification and cannot be converted in a simple manner, e.g., by spray drying of the entire reaction mixture, into a product which can be commercialised directly. For these reasons phosphorylation using phosphorus oxychloride is a process which has little attraction economically and ecologically. The alternative process, i.e. phosphorylation using polyphosphates, yields ascorbic acid 2-polyphosphate as the primary product, for example ascorbic acid 2-triphosphate when sodium trimetaphosphate is used. The ascorbic acid 2-polyphosphates can be degraded to the monophosphate by an excess of base. The ratio of ascorbic acid 2-monophosphate to ascorbic acid 2-diphosphate and higher phosphates is influenced by the amount of base which is used and the other reaction conditions. A disadvantage of this process is that a very large amount of phosphorylating agent, e.g., at least 1 mol of sodium trimetaphosphate per mol of ascorbic acid, is required. Moreover, when the product should contain relatively little ascorbic acid polyphosphates and more ascorbic acid 2-monophosphate, a large amount of base, e.g., calcium hydroxide, must be used. Accordingly, the product contains a large amount of inorganic phosphates; the content of ascorbic acid equivalents in a dried product amounts to a maximum of about 25 weight percent. The course of the process described in U.S. Pat. No. 5,110,950, insofar as it is used for the manufacture of the monophosphate, will be evident from Reaction Scheme 1 hereinafter in which, for the purpose of a clear and simple presentation, sodium ascorbate, sodium trimetaphosphate (the preferred phosphorylating agent) and calcium hydroxide (base) are used:

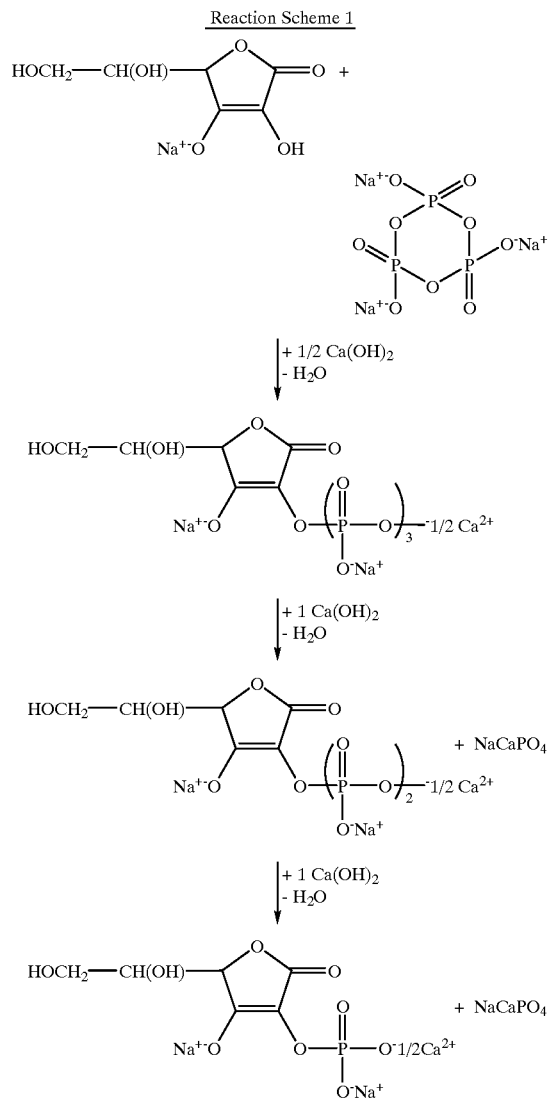

In this process sodium ascorbate is reacted with sodium trimetaphosphate in a molar ratio of 1:1 under the influence of a total of 2.5 mol of calcium hydroxide in order to produce 1 mol of ascorbic acid 2-monophosphate after three steps. Thereby, 2 mol of sodium calcium phosphate are liberated, the presence of which in the overall product is seen to be a disadvantage.

SUMMARY OF THE INVENTION

The present invention provides a method of making alkali metal and alkaline earth metal salts of L-ascorbic acid 2-monophosphate of the general formula

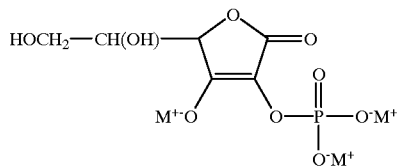

and mixtures thereof, wherein each M+ is an ion selected from the group consisting of an alkali metal ion and the molar equivalent of an alkaline earth metal ion, substantially without the presence of L-ascorbic acid polyphosphate comprising forming a reaction mixture containing a concentrated aqueous solution of an alkali metal or alkaline earth metal salt of L-ascorbic acid of the general formula

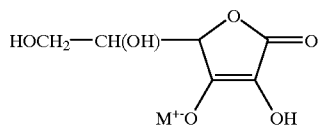

wherein M+ has the significance given above,
and a L-ascorbic acid 2-polyphosphate of the general formula

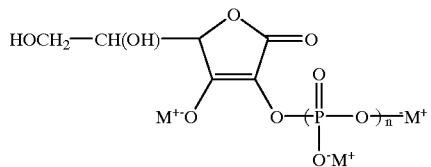

wherein M+ has the significance given above and n signifies an integer from 2, wherein the amount of the L-ascorbic acid salt of formula III is in molar excess relative to the amount of L-ascorbic acid 2-polyphosphate of formula II, and reacting the alkali metal or alkaline earth metal salt of L-ascorbic acid with the polyphosphate in the reaction mixture in the presence of an alkaline earth metal hydroxide to produce the monophosphate salt, the reaction being carried out until all of the polyphosphate is consumed in the reaction, and the pH of the reaction mixture is maintained from about 8 to about 11 through the presence of the alkaline earth metal hydroxide.

In accordance with the method of the present invention the reaction mixture can be formed by producing the L-ascorbic acid 2-polyphosphate of formula II in situ in the reaction mixture through the addition of a phosphorylating agent prior to carrying out the reaction; in this case the L-ascorbic acid salt of formula III is phosphorylated by the phosphorylating agent to afford the L-ascorbic acid 2-polyphosphate of formula II. Alternatively, the reaction mixture can be formed by adding the L-ascorbic acid 2-polyphosphate of formula II to the reaction mixture.

By this method the required amounts of phosphorylating agent and base can be drastically reduced and the major disadvantages of the known processes can be eliminated.

DETAILED DESCRIPTION OF THE INVENTION

The present invention provides a novel method for making alkali metal and alkaline earth metal salts of L-ascorbic acid 2-monophosphate from a L-ascorbic acid salt, a L-ascorbic acid 2-polyphosphate and an alkaline earth metal hydroxide as the base wherein the monophosphate salt is substantially free of polyphosphate, i.e., wherein the reaction is carried out until substantially all of the polyphosphate is consumed in the reaction such that the final product produced in the reaction mixture contains polyphosphate in an amount from a trace amount up to about less than 7% polyphosphate by weight of the final product.

In accordance with the present invention, the method of making alkali metal and alkaline earth metal salts of L-ascorbic acid 2-monophosphate of the general formula

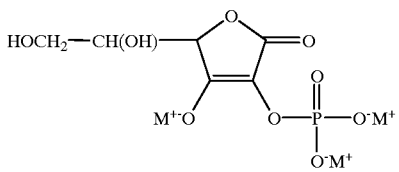

and mixtures thereof, wherein each M+ is an ion selected from the group consisting of an alkali metal ion and the molar equivalent of an alkaline earth metal ion,
in a reaction mixture substantially without the presence of L-ascorbic acid polyphosphate comprises forming a reaction mixture containing a concentrated aqueous solution of an alkali metal or alkaline earth metal salt of L-ascorbic acid of the general formula

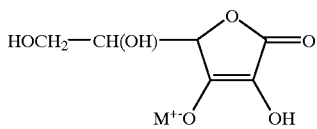

wherein M+ has the significance given above, and a L-ascorbic acid 2-polyphosphate of the general formula

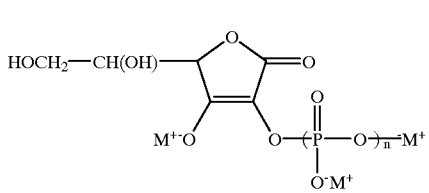

wherein M+ has the significance given above and n signifies an integer from 2,
wherein the amount of the L-ascorbic acid salt of formula III is in molar excess relative to the amount of L-ascorbic acid 2-polyphosphate of formula II, reacting the alkali metal or alkaline earth metal salt of L-ascorbic acid with the polyphosphate in the reaction mixture in the presence of an alkaline earth metal hydroxide to produce the monophosphate salt, the reaction being carried out until substantially all of the polyphosphate is consumed in the reaction, and the pH of the reaction mixture is maintained from about 8 to about 11 through the presence of the alkaline earth metal hydroxide.

In accordance with the method of the present invention, the reaction mixture can be formed by producing the L-ascorbic acid 2-polyphosphate of formula II in situ in the reaction mixture through the addition of a phosphorylating agent prior to carrying out the reaction; said phosphorylating agent phosphorylates the L-ascorbic acid salt of formula III to the L-ascorbic acid 2-polyphosphate of formula II. Alternatively, the reaction mixture can be formed by adding the L-ascorbic acid 2-polyphosphate of formula II to the reaction mixture.

To obtain the alkali metal and alkaline earth metal salts of L-ascorbic acid 2-monophosphate wherein the polyphosphate has been substanially consumed, the L-ascorbic acid salt of formula III must always be present in the reaction mixture in a molar excess relative to the amount of L-ascorbic acid 2-polyphosphate of formula II, and the reaction is allowed to go to completion while maintaining the pH at from about 8 to about 11 until all of the polyphosphate is consumed. The reaction mixture of the present invention is formed by initially preparing an aqueous solution of the L-ascorbic acid salt which is as concentrated as possible (virtually saturated), e.g. by treating a concentrated aqueous solution of ascorbic acid with alkali hydroxide, e.g., sodium hydroxide. The subsequent addition of the (separately produced) L-ascorbic acid 2-polyphosphate or the phosphorylating agent (for the in situ production of the polyphosphate), e.g., sodium trimetaphosphate, and the base, e.g., calcium hydroxide, to the concentrated aqueous solution of the L-ascorbic acid salt is preferably spread over the entire reaction period such that the L-ascorbic acid 2-polyphosphate (optionally produced in situ) and the L-ascorbic acid salt react immediately with one another under the prevailing alkaline conditions. To maintain the required alkaline conditions, the pH value is held within the range of about 8 to about 11 by the addition of the base.

The phosphorylation of L-ascorbic acid or a salt thereof is a conventional reaction. However, in prior methods when such phosphorylations occur, the monophosphates are produced in a mixture of polyphosphates. In accordance with the present invention, conventional methods for phosphorylating L-ascorbic acid salts can be regulated in the aforementioned manner, to produce monophosphate salts of L-ascorbic acid that are substantially free of polyphosphate. A stepwise transfer of one phosphate group from the polyphosphate to the L-ascorbic acid salt takes place until the polyphosphate has been substantially consumed and the monophosphate salt is produced. Thus, in carrying out the method of the present invention, conventional reaction conditions for phosphorylation of L-ascorbic acid or salts thereof can be utilized.

In accordance with the present invention, the "alkali metal ion" is preferably a sodium or potassium ion. A sodium ion is most preferred. Preferably, the alkaline earth metal ion is a calcium ion or a magnesium ion, the former being preferred. In this case and taking into consideration its divalency, the alkaline earth metal ion is represented in each case as a half ion, so that, for example, a calcium ion $M^+$ in formula I, II or III is presented as ½ $Ca^{2+}$. Although the ions $M^+$ in formulas I, II and III can be the same or different, the individual meanings depend on the nature of the L-ascorbic acid salt of formula III used for the production of the polyphosphate of formula II and of the phosphorylating agent as well as on the nature of the alkaline base which is used, whereby, inter alia, ion exchange also plays a role. Preferably, the same base used for the production of the polyphosphate is used as the base in the process in accordance with the invention. This can be illustrated on the basis of an example: when the sodium salt of L-ascorbic acid (of formula III in which $M^+$ signifies $Na^+$) is used, sodium trimetaphosphate of the formula

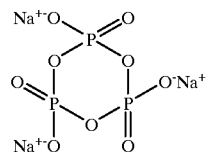

is used as the phosphorylating agent and calcium hydroxide [$Ca(OH)_2$] is used as the base (all preferred reactants), formulas I, II and III can be represented, inter alia and simply, as follows:

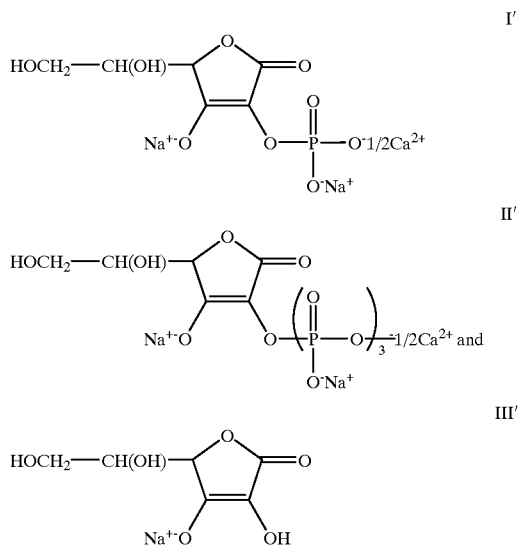

respectively. From this it will be evident that n is also dependent on the nature of the phosphorylating agent: for example, n signifies 3 when sodium trimetaphosphate is used as the phosphorylating agent and signifies 6 when sodium hexametaphosphate is used for this purpose. Furthermore, the product of formula I or I' can occur as a mixture of different alkali metal and alkaline earth metal salts of L-ascorbic acid 2-monophosphate.

The course of the method in accordance with a preferred embodiment of the present invention is evident from Reaction Scheme 2 hereinafter in which, for the purpose of a clear and simplified presentation, L-ascorbic acid sodium salt of formula III' is used, sodium trimetaphosphate is used as the phosphorylating agent (for the production of L-ascorbic acid 2-polyphosphate of formula II') and calcium hydroxide is used as the base. Thus, there is produced a L-ascorbic acid 2-monophosphate which features, inter alia, molecules of formula I':

Reaction Scheme 2

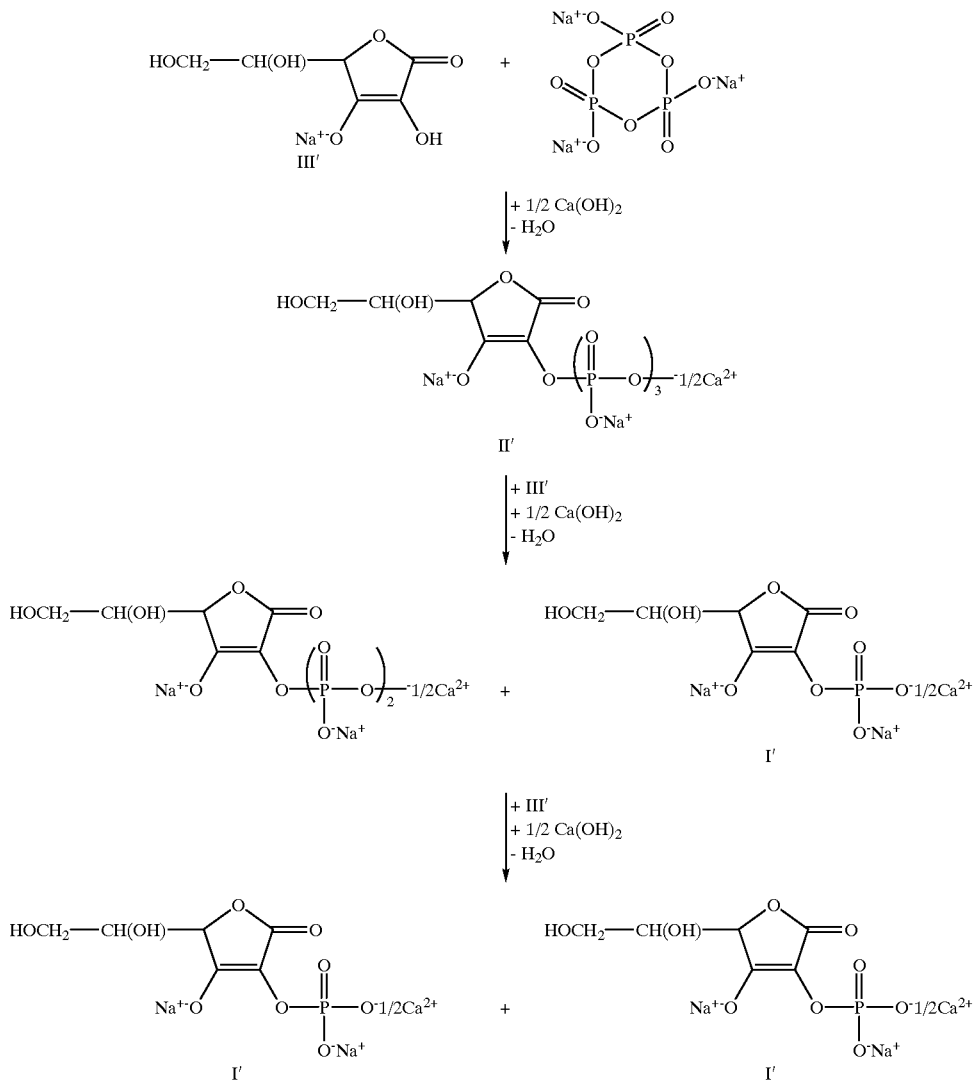

The production of the L-ascorbic acid 2-polyphosphate of formula II can be effected in advance (separately) or in situ, preferably in situ. Starting from a L-ascorbic acid 2-polyphosphate of formula II, produced separately or in situ, the molar ratio of L-ascorbic acid salt of formula III to L-ascorbic acid 2-polyphosphate of formula II conveniently amounts to about n-1:1, the deviation from this ratio preferably not amounting to more than about 30%.

Where it is desired to produce the L-ascorbic acid 2-polyphosphate of formula II separately, this can be effected in a manner known per se, conveniently according to the method described in U.S. Pat. No. 5,110,950. The reaction product can be isolated (evaporation) or used immediately as an aqueous solution for the further reaction (with the L-ascorbic acid salt of formula III). The preferred phosphorylating agent for the separate (and also for the in situ) production of the L-ascorbic acid 2-polyphosphate is sodium trimetaphosphate, this polyphosphate having three phosphate groups

in the molecule (n=3). Higher metaphosphates, e.g., the sodium hexametaphosphate mentioned above, or polyphosphoric acid can, in principal also be used.

With respect to the in situ production of the L-ascorbic acid 2-polyphosphate, the phosphorylating agent is conveniently added to the concentrated solution of the L-ascorbic acid salt. The phosphorylating agent, e.g., sodium trimetaphosphate, can be added, for example, as an aqueous solution or as a solid, the latter method of addition being preferred. Conveniently, the addition of the base, e.g., calcium hydroxide, is also effected either separately or in a mixture with the phosphorylating agent. The simultaneous addition of the phosphorylating agent and the base, especially by the addition of a mixture of the two, is preferred.

Since the reaction medium should be as concentrated as possible, in the case of the in situ production of the L-ascorbic acid 2-polyphosphate, the phosphorylating agent and the base are advantageously added as solids. The pH value can be adjusted continuously by appropriate dosage of the base, even when this is in admixture with the phosphorylating agent, namely by periodically fixing the ratio of phosphorylating agent to base. Moreover, the velocity of the addition of phosphorylating agent and base is preferably adjusted such that no L-ascorbic acid 2-polyphosphate precipitates; the reaction is accordingly carried out in such a manner that the polyphosphate reacts further as rapidly as possible with the L-ascorbic acid salt via the (in each case) less polyphosphorylated L-ascorbic acid salt, e.g., the L-ascorbic acid 2-diphosphate, to give the L-ascorbic acid 2-monophosphate. In practice, for this purpose it is preferred that the phosphorylating agent is added rather rapidly at the beginning and rather slowly towards the end of the reaction. Moreover, it is recommended to guarantee a good intermixing of the reactants in order that the added solid starting materials are brought rapidly into an intensive contact with the liquid reaction medium.

The L-ascorbic acid salt used in the process in accordance with the invention is preferably an alkali metal salt, especially the sodium salt (III=III'), since such salts are especially water-soluble. Alkali metal salts of ascorbic acid can be obtained, for example, in advance by lactonization of 2-keto-L-gulonic acid esters, e.g., methyl 2-keto-L-gulonate, with sodium bicarbonate, sodium carbonate or sodium hydroxide. In each case there is produced an aqueous solution of the salt, preferably a solution which is almost saturated at the reaction temperature.

To form the reaction mixture in accordance with the method of the present invention, the amount of polyphosphate used is chosen such that the amount of L-ascorbic acid salt in the reaction mixture is in molar excess to the amount of polyphosphate, and the final content of L-ascorbic acid 2-monophosphate in the end product is as high as possible, i.e. as much L-ascorbic acid salt as possible is consumed. As stated above, starting from a L-ascorbic acid 2-polyphosphate of formula II, produced separately or in situ, the molar ratio of L-ascorbic acid salt of formula III to L-ascorbic acid 2-polyphosphate of formula II is about n-1:1, the deviation from this ratio preferably not amounting to more than 30%. For example, when a phosphorylating agent such as sodium trimetaphosphate is used to form the polyphosphate in situ, about 0.3 to about 0.5 mol, preferably about 0.35 to about 0.45 mol, of this phosphorylating agent is used per mol of L-ascorbic acid salt.

In order to adjust the pH value within the range of about 8 to about 11, in the case of the in situ production of the L-ascorbic acid 2-polyphosphate conveniently about 0.5 to about 0.8 mol, preferably about 0.55 to about 0.65 mol, of alkaline earth metal hydroxide is added per mol of L-ascorbic acid salt. Calcium hydroxide is the preferred alkaline earth metal hydroxide. Since the alkaline earth metal hydroxides are not particularly water-soluble, the alkaline earth metal hydroxide can be added as a suspension in water. However, the alkaline earth metal hydroxide is preferably added as a solid, especially, as mentioned above, in admixture with the phosphorylating agent (in situ production of the L-ascorbic acid 2-polyphosphate).

During the reaction the pH value preferably amounts to about 9 to about 10. The reaction is too slow at too low a pH value. A pH value which is too high is also disadvantageous. The pH value should not be substantially higher than 10, in any case not higher than about 11, since the L-ascorbic acid salt has only a low stability under strongly alkaline conditions and since inorganic phosphates are increasingly formed. In the case of too high a pH value L-ascorbic acid 2-polyphosphate and less phosphorylated L-ascorbic acid salt, e.g., L-ascorbic acid 2-diphosphate, are converted into L-ascorbic acid 2-monophosphate by cleavage of phosphate groups with the base and not by reaction with L-ascorbic acid salt; thereby the content of inorganic salts in the end product increases, which is clearly a disadvantage.

The process in accordance with the invention is conveniently effected at temperatures in the range of about 20° C. to about 80° C., preferably at temperatures in the range of about 40° C. to about 60° C. In general, the temperature is gradually raised in the course of the process, for example from about 40° C. initially to about 60–70° C. towards the end of the reaction. After completion of the reaction the temperature is advantageously lowered in order to stop the reaction.

The reaction time required to achieve a satisfactory yield of L-ascorbic acid 2-monophosphate of formula I depends on various factors, especially the reaction temperature, the pH value, the amount of water in the reaction mixture as well as the stirring intensity. In general, it is preferred to add the L-ascorbic acid 2-polyphosphate rather slowly or to produce it in situ rather than to add it rapidly. When the pH value and the temperature are not unnecessarily high and an excessive amount of oxygen is not present, a somewhat long reaction time is not disadvantageous. Reaction times of about 1 to about 4 hours, preferably of about 1½ to about 2½ hours, are typical.

After completion of the reaction the mixture obtained can be cooled, for example, to about 30–40° C., and diluted with water until the viscosity is suitable for a spray drying, for example, about 100 mPa, and finally spray dried. When spray drying is carried out, practically no byproducts occur which subsequently have to be disposed of. Advantageous in the process accordance with the invention are the considerable avoidance of byproducts and the high content (high yield) of desired L-ascorbic acid 2-monophosphate of formula I. By this means the raw material costs and the energy costs in the spray drying are reduced to a minimum.

The process in accordance with the invention is illustrated by the following Examples in which, with the exception of Example 2, the content of L-ascorbic acid 2-monophosphate and 2-polyphosphates is in each case given in L-ascorbic acid equivalents:

EXAMPLE 1

Reaction of L-ascorbic Acid 2-triphosphate (main constituent of the so-designated mixture used) with Sodium Ascorbate 67.3 g (340 mmol) of sodium ascorbate are added to 50 ml of water in a 750 ml double jacketed reaction vessel while stirring and under a nitrogen atmosphere at 60° C. and thereby dissolved for the most part. The pH value is adjusted to 9.5 with 3.7 g of calcium hydroxide. 87 g of solid L-ascorbic acid 2-triphosphate (HPLC analysis: 4.3% ascorbic acid, 0.5% L-ascorbic acid as the 2-monophosphate, 1.4% L-ascorbic acid as the 2-diphosphate as well as 21.1% L-ascorbic acid as the 2-triphosphate) are added portionwise in the course of 2 hours, 58 g being added during the first hour and 29 g during the second hour. The pH value is held at 9.5 by the addition of 33.9 g of calcium hydroxide. Sufficient water (a total of 50 g) is added in order that the suspension can always be stirred well. After completion of the reaction the batch is evaporated to dryness (water content: 10.5%). HPLC analysis of the dried product indicates 10.9% (residual, non-phosphorylated) L-ascorbic acid, 34.5% L-ascorbic acid as the 2-monophosphate and 0.6% L-ascorbic acid as the 2-diphosphate. L-Ascorbic acid 2-triphosphate can no longer be detected.

EXAMPLE 2 a) Separate Production of a L-ascorbic Acid 2-polyphosphate Solution 150 ml of water are cooled to 0° C. in a 500 ml double jacketed reaction vessel. Then 114.44 g of sodium trimetaphosphate are added while stirring. The pH value is adjusted to 11 with slaked lime (a 20% suspension of calcium hydroxide in water), which gives the sodium trimetaphosphate solution.

67.32 g of sodium ascorbate are dissolved in 150 ml of water. The pH value is adjusted to 11 with slaked lime. Then the solution is cooled to 0° C., which gives the sodium ascorbate solution.

The sodium ascorbate solution is added rapidly to the sodium trimetaphosphate solution. The temperature is increased to 30° C. in the course of 2 hours. The pH value is held at 11 with slaked lime. After 2 hours the batch is cooled to 0° C., which gives the L-ascorbic acid 2-polyphosphate solution.

b) Reaction of L-ascorbic Acid 2-polyphosphate with Sodium Ascorbate 134.64 g of sodium ascorbate are dissolved in 100 ml of water at 60° C. while stirring and under a nitrogen atmosphere in a 500 ml double jacketed reaction vessel. The pH value is adjusted to 10.5 with slaked lime. Half of the L-ascorbic acid 2-polyphosphate solution is added within one hour and the remainder is added within two hours. The pH value is held at 10.5 with slaked lime. During the last two hours water is distilled off under reduced pressure. After completion of the reaction the batch is neutralized to pH 7 with sulphuric acid and diluted with 300 ml of water. HPLC analysis indicates the following distribution of the L-ascorbic acid: 14.3% non-phosphorylated, 76.2% as the monophosphate, 7.6% as the diphosphate, <1% as the triphosphate and <2% as additional L-ascorbic acid 2-polyphosphates.

EXAMPLE 3

In situ Production of L-ascorbic Acid 2-polyphosphate and its Reaction with Sodium Ascorbate 100 g of water are placed in a 500 ml double jacketed reaction vessel. Thereafter it is degassed by the application of a vacuum. The vacuum is broken with nitrogen and 176 g (1 mol) of ascorbic acid are added. The ascorbic acid is neutralized with 141.6 g of 28% sodium hydroxide solution while stirring and under reduced pressure. The vacuum is broken with nitrogen and the temperature is adjusted to 50° C. A mixture of 142.8 g (0.467 mol) of sodium trimetaphosphate and 51.9 g (0.7 mol) of calcium hydroxide is added within 2 hours under nitrogen. The addition is rapid at the beginning of the reaction and slow towards the end of the reaction. The reaction mixture is stirred for 60 minutes, neutralized with 5.2 g of 98% sulphuric acid and diluted with 300 g of water. An aliquot (about 10 ml) is removed from the reaction mixture and evaporated to dryness under reduced pressure. HPLC analysis indicates 1.3% L-ascorbic acid, 34.3% L-ascorbic acid as the 2-monophosphate and 3.5% L-ascorbic acid as the 2-diphosphate, a total of 42% phosphorylated ascorbic acid.

EXAMPLES 4–7

These Examples were carried out analogously to Example 3, but under varying reaction conditions. In particular, the amount of sodium trimetaphosphate was reduced gradually. The results obtained are compiled in the following Table.

TABLE

| Example | 4 | 5 | 6 | 7 |
|---|---|---|---|---|
| Water (g) | 50 | 50 | 50 | 50 |
| ASC (g) | 176 | 176 | 176 | 176 |
| NaOH 28% (g) | 163.5 | 166 | 163.5 | 163.5 |
| STMP (g) | 132.6 | 112.2 | 102 | 91.8 |
| Ca(OH)$_2$ (g) | 37 | 37 | 37 | 33.3 |
| H$_2$SO$_4$ (g) | 4 | 8.8 | 10.4 | 8.9 |
| Water (g) | 200 | 200 | 200 | 200 |
| Reaction solution (g) | 763.1 | 750 | 738.9 | 723.5 |
| Temperature (° C.) | 40–60 | 40 | 40–60 | 40–60 |
| pH value of the NaASC solution | 9.9 | 10 | 10 | 10 |
| STMP/Ca(OH)$_2$ addition in | 2 h | 4 h | 2 h | 2 h |
| second stirring | 0.25 h | 1 h | 0.25 h | 0.25 h |
| HPLC analysis (ASC equivalents): nonphosphorylated ASC (%) | 5 | 7.1 | 8.7 | 11.4 |
| ASC as the monophosphate (%) | 31.6 | 37.9 | 39.4 | 38.1 |
| ASC as the diphosphate (%) | 6.2 | 2.5 | 1.2 | 0.9 |
| ASC phosphates total (%) | 39.3 | 41.5 | 41.6 | 39.6 |
| ASC total (%) | 44.3 | 48.6 | 50.3 | 51 |

ASC = L-Ascorbic acid
STMP = Sodium trimetaphosphate
NaASC = Sodium ascorbate

EXAMPLE 8

Fluidized Bed Drying of the Product 165 g of water are placed in a 750 ml double jacketed reaction vessel. Thereafter it is degassed by the application of a vacuum. The vacuum is broken with nitrogen and 176 g (1 mol) of ascorbic acid are added. 88.4 g of 5 sodium hydroxide solution are added while stirring. The pH value is then 9.1. The temperature is adjusted to 40° C. A mixture of 132.6 g (0.433 mol) of sodium trimetaphosphate and 44.45 g (0.6 mol) of calcium hydroxide is added uniformly within two hours under nitrogen and the temperature in the reactor is increased to 60° C. The mixture is stirred for 30 minutes, cooled to 40° C. and diluted with 200 g of water. Then the reaction mixture is evaporated under reduced pressure. The resulting solid product is ground and dried in a fluidized bed dryer with 10 m$^3$ of hot air at 100° C. for 30 minutes. There are obtained 364 g of beige-brown powder having 6.3% residual moisture. HPLC analysis indicates 3% L-ascorbic acid, 33.2% L-ascorbic acid as the 2-monophosphate and 3.8% L-ascorbic acid as the 2-diphosphate, a total of 37.6% phosphorylated ascorbic acid.

EXAMPLE 9

Spray Drying of the Product 100 g of water are placed in a 500 ml double jacketed reaction vessel. Thereafter it is degassed by the application of a vacuum. The vacuum is broken with nitrogen and 176 g (1 mol) of ascorbic acid are added. The ascorbic acid is neutralized with 142.8 g of 28% sodium hydroxide solution while stirring and under reduced pressure. The pH value is adjusted to 10 by the addition of 18.6 g of calcium hydroxide. The vacuum is broken with nitrogen and the temperature is adjusted to 40° C. A mixture of 132.6 g (0.433 mol) of sodium trimetaphosphate and 48.2 g (0.65 mol) of calcium hydroxide is added within 4 hours under nitrogen. The reaction mixture is stirred for 90 minutes, neutralized with 7.1 g of 98% sulphuric acid and diluted with 300 g of water. The entire reaction mixture is spray-dried in a laboratory spray tower. According to HPLC analysis the powder contains 3.7% L-ascorbic acid, 38% L-ascorbic acid as the 2-monophosphate and 2.8% L-ascorbic acid as the 2-diphosphate, a total of 46.9% of phosphorylated ascorbic acid.

EXAMPLE 10
Use of Sodium Ascorbate from the Lactonization of Methyl 2-keto-L-gulonate 208.4 g of methyl 2-keto-L-gulonate are dissolved in 500 g of methanol and the solution is heated to boiling while stirring. 52 g of sodium carbonate are added in the course of 2 hours. The pH value is then 8. The mixture is stirred for 30 minutes, cooled to 40° C. and the precipitated sodium ascorbate is filtered off and washed with 100 g of methanol. The moist sodium ascorbate is dried in a drying oven at 40° C. under reduced pressure. There are obtained about 198.1 g of crude sodium ascorbate with a content of pure sodium ascorbate of about 94%.

198.1 g of crude sodium ascorbate are dissolved in 230 g of water at 40° C. in a 500 ml double jacketed reaction vessel. The temperature is increased to 60° C. within 2 hours and a mixture of 132.6 g (0.433 mol) of sodium trimetaphosphate and 44.45 g (0.6 mol) of calcium hydroxide is added. The mixture is stirred for 30 minutes, cooled to 40° C. and diluted with 200 g of water. The entire reaction mixture is evaporated as rapidly as possible on a rotary evaporator under reduced pressure at a bath temperature of 60° C. and the residue is ground in a mortar and subsequently dried in a drying oven at 60° C. under reduced pressure (weight yield: 375.8 g). The water content is 6.7%. According to HPLC analysis the powder contains 3.7% L-ascorbic acid, 31.0% L-ascorbic acid as the 2-monophosphate, 3.6% L-ascorbic acid as the 2-diphosphate as well as 1.9% L-ascorbic acid as the 2-triphosphate.

EXAMPLE 11
Use of Sodium Ascorbate from the Lactonization of Methyl 2-keto-L-gulonate without Isolation of the Sodium Ascorbate 208.4 g of methyl 2-keto-L-gulonate are dissolved in 500 g of methanol and the solution is heated to boiling while stirring. 52 g of sodium carbonate are added in the course of 2 hours, during which the pH value does not rise substantially above 8. The mixture is stirred for a further 30 minutes, diluted with 230 g of water and the majority of the methanol is distilled off over a Vigreux column. The distillation residue (439 g) is cooled to 40° C. Then the temperature is increased from 40° C. to 60° C. in the course of 2 hours under nitrogen and a mixture of 132.6 g of sodium trimetaphosphate and 44.45 g of calcium hydroxide is added. The mixture is stirred for a further 30 minutes. The entire reaction mixture is evaporated as rapidly as possible under reduced pressure at a bath temperature of 60° C. and the residue is ground in a mortar and subsequently dried in a drying oven at 60° C. under reduced pressure (weight yield: 388 g). The water content is 9%. According to HPLC analysis the powder contains 3.6% L-ascorbic acid, 30.2% L-ascorbic acid as the 2-monophosphate, 4.9% L-ascorbic acid as the 2-diphosphate as well as 0.9% L-ascorbic acid as the 2-triphosphate.

EXAMPLE 12
Use of Potassium Hydroxide as the Base 175.6 g of water are placed in a 750 ml double jacketed reaction vessel and degassed by the application of a vacuum. The vacuum is broken with nitrogen and 176 g (1 mol) of ascorbic acid are added. The ascorbic acid is neutralized with 113.2 g of 55.9% potassium hydroxide solution while stirring and under reduced pressure. The vacuum is broken with nitrogen and the temperature is adjusted to 40° C. The temperature is increased from 40° C. to 60° C. within 2 hours under a nitrogen atmosphere and a mixture of 132.6 g (0.433 mol) of sodium trimetaphosphate and 48.2 g (0.65 mol) of calcium hydroxide is added. The mixture is stirred for a further 15 minutes and diluted with 200 g of water. The entire reaction mixture is evaporated as rapidly as possible under reduced pressure at a bath temperature of 60° C., and the residue is ground in a mortar and subsequently dried in a drying oven at 60° C. under reduced pressure (weight yield: 391.7 g). The water content is 5%. According to HPLC analysis the powder contains 4.7% L-ascorbic acid, 32.5% L-ascorbic acid as the 2-monophosphate, 3.9% L-ascorbic acid as the 2-diphosphate as well as 1.1% L-ascorbic acid as the 2-triphosphate.

We claim:
1. A method of making alkali metal and alkaline earth metal salts of L-ascorbic acid 2-monophosphate of the general formula

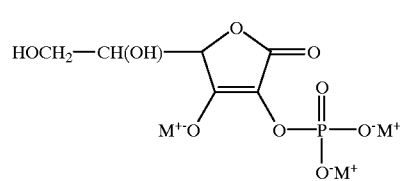

I and mixtures thereof, wherein each $M^+$ is an ion selected from the group consisting of an alkali metal ion and the molar equivalent of an alkaline earth metal ion, substantially without the presence of L-ascorbic acid polyphosphate comprising
forming a reaction mixture containing a concentrated aqueous solution of an alkali metal or alkaline earth metal salt of L-ascorbic acid of the general formula

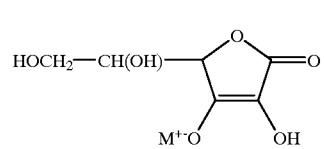

III wherein $M^+$ has the significance given above, and a L-ascorbic acid 2-polyphosphate of the general formula

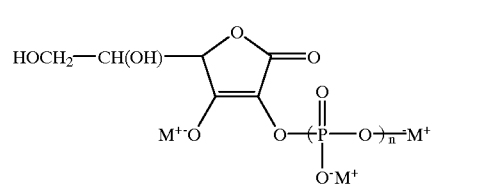

II wherein $M^+$ has the significance given above and n signifies an integer from 2,
wherein the amount of the L-ascorbic acid salt of formula III is in molar excess relative to the amount of L-ascorbic acid 2-polyphosphate of formula II; and
reacting said alkali metal or alkaline earth metal salt of L-ascorbic acid with said polyphosphate in said reaction mixture in the presence of an alkaline earth metal hydroxide to produce said monophosphate salt, said reaction being carried out until substantially all of the polyphosphate is consumed in the reaction, and the pH of the reaction mixture is maintained from about 8 to about 11 through the presence of the alkaline earth metal hydroxide.

2. The method of claim 1, wherein the amount of polyphosphate in the final monophosphate salt product is less than about 7% by weight of the final monophosphate salt product.

3. The method of claim 1, wherein the base is calcium hydroxide.

4. The method of claim 1, wherein said reaction mixture is formed by producing the L-ascorbic acid 2-polyphosphate of formula II in situ in the reaction mixture through the addition of a phosphorylating agent prior to carrying out the reaction.

5. The method of claim 4, wherein the phosphorylating agent is selected from the group consisting of sodium trimetaphosphate, sodium hexametaphosphate and polyphosphoric acid.

6. The method of claim 4, wherein the phosphorylating agent is sodium trimetaphosphate and the base is calcium hydroxide.

7. The method of claim 1, wherein the reaction mixture is formed by adding the L-ascorbic acid 2-polyphosphate of formula II to the reaction mixture.

8. The method of claim 1, wherein the L-ascorbic acid 2-polyphosphate has the formula

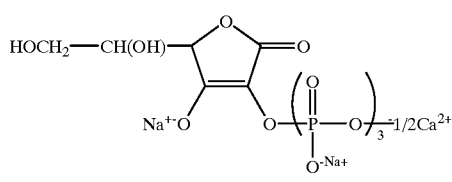

II' the alkali metal salt of L-ascorbic acid used has the formula

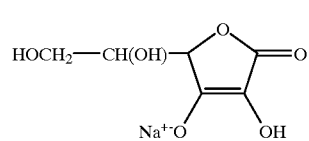

III' and calcium hydroxide is used as the base.

9. The method of claim 4, wherein about 0.5 to about 0.8 mol of alkaline earth metal hydroxide is used per mol of L-ascorbic acid salt of formula III.

10. The method of claim 9, wherein about 0.55 to about 0.65 mol of alkaline earth metal hydroxide is used per mol of L-ascorbic acid salt of formula III.

11. The method of claim 4, wherein about 0.3 to about 0.5 mol of sodium trimetaphosphate as the phosphorylating agent is used per mol of L-ascorbic acid salt of formula III.

12. The method of claim 11, wherein about 0.35 to about 0.45 mol of sodium trimetaphosphate as the phosphorylating agent is used per mol of L-ascorbic acid salt of formula III.

13. The method of claim 1, wherein the reaction is effected at temperatures in the range of about 20° C. to about 80° C.

14. The method of claim 13, wherein the reaction is effected at temperatures in the range of about 40° C. to about 60° C.

15. The method of claim 1, wherein the pH value is about 9 to about 10.

16. The method of claim 1, further comprising, cooling and diluting the reaction mixture containing the L-ascorbic acid 2-monophosphate salt of formula I to a viscosity suitable for spray drying, and spray drying the reaction mixture.

* * * * *